Figure 1:
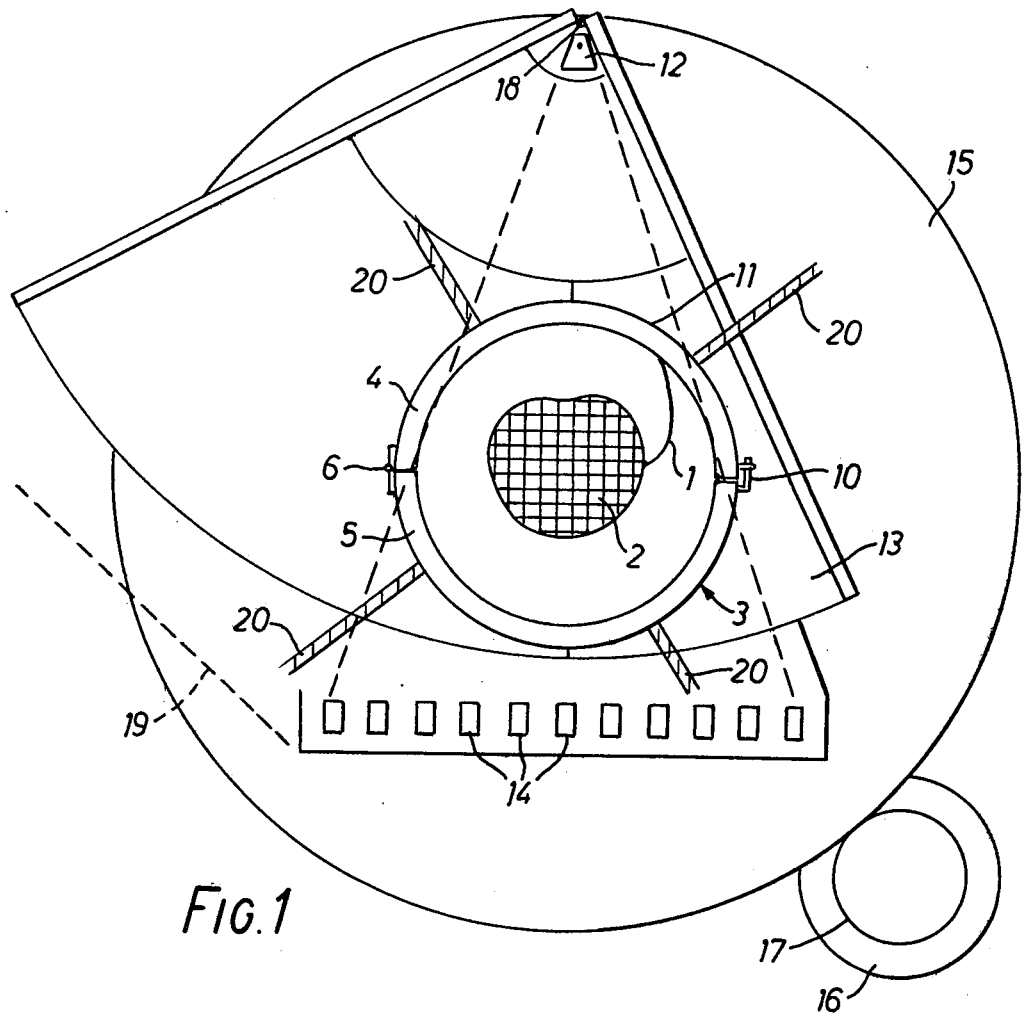

United States Patent [19]
Hounsfield

[11] 3,937,963
[45] Feb. 10, 1976

[54] RADIOGRAPHIC APPARATUS

[75] Inventor: Godfrey Newbold Hounsfield, Newark, England

[73] Assignee: E M I Limited, Hayes, England

[22] Filed: June 4, 1974

[21] Appl. No.: 476,300

[30] Foreign Application Priority Data
June 5, 1973 United Kingdom.................... 26811
Feb. 14, 1974 United Kingdom................. 6809/74

[52] U.S. Cl. ............... 250/363; 250/447; 250/451; 250/505
[51] Int. Cl.²... G01T 1/20; G02B 5/00; G21K 5/08; G21K 5/06
[58] Field of Search ....... 178/DIG. 5; 250/505, 439, 250/451, 447, 446, 445 T, 445, 444, 363

[56] References Cited
UNITED STATES PATENTS
1,980,848  11/1934  Cass.................................. 250/451
3,486,022  12/1969  Matuda et al....................... 250/447

Primary Examiner—James W. Lawrence
Assistant Examiner—T. N. Grigsby
Attorney, Agent, or Firm—Fleit & Jacobson

[57] ABSTRACT

Apparatus for examining a body by means of penetrating radiation includes a source of the radiation, disposed to irradiate the body, and detector means, responsive to the radiation, disposed to receive radiation emergent from the body. The source and detector means are scanned relative to the body, the scanning motion including a rotation of the source and detector means around the body. An attenuating mass is disposed between the source and detector means and rotates therewith so as to present substantially the same profile to the radiation when the source and detector means assume different angular positions with respect to the body.

9 Claims, 9 Drawing Figures

RADIOGRAPHIC APPARATUS

This invention relates to apparatus for examining a body by means of penetrating radiation, such as X-radiation, and it relates in particular to such apparatus for examining human patients.

In our U.S. Pat. No. 3,778,614 apparatus is described for examining this sectional slices of the human body by means of penetrating radiation, and for reconstructing an image of the variable transmission or absorption of the elements of the section of the body, with respect to said radiation. One form of apparatus according to this British Patent Specification is now in use for examining the human head. In this apparatus, accurate positioning of the head relative to the source of radiation, and to the means for detecting the radiation after passage through the head, is necessary to ensure accurate image reconstruction. The required accuracy of positioning is achieved by supporting the head in a pouched flexible member forming one wall of a water reservoir. When the reservoir is filled with water, the flexible member serves to hold the head firmly but gently. The source of radiation and the detecting means are scanned relative to the head supported in the pouched member, the scanning movements including a step by step rotation of the source of radiation and detecting means. The water reservoir, apart from its flexible wall, participates in this rotation, and the reservoir in addition to its function of supporting the head, acts as an attenuator serving in all angular positions to compensate substantially for variations in the path length for the radiation across the width of the head.

The expedient used in the case of a head machine however gives rise to difficulties if other parts of the body have to be examined. One reason for such difficulties is that it is impracticable to use a flexible pouched member for support if for example, the torso or other intermediate parts of the body have to be examined. Moreover provision has to be made to accommodate a much greater variety of sizes than in the case of the head.

The principal object of the present invention is to reduce the difficulties indicated in the preceding paragraph.

According to the present invention there is provided apparatus for examining the body of a patient by means of penetrating radiation comprising:
a. a ring-shaped locating structure adapted to enclose the part of the patient to be examined,
b. a source of penetrating radiation,
c. a detecting means sensitive to the radiation,
d. a scanning structure, which is rotatable about an axis passing through the part of the patient enclosed by said locating structure, supporting said source and said detecting means so the source can project radiation through the said part of the patient to be received by the detecting means,
e. means for rotating said scanning structure about said axis so that the radiation can be projected through the body from a plurality of different directions in a plane substantially perpendicular to the said axis and,
f. an attenuating mass not attached to and adapted to rotate around said locating structure on rotation of said scanning structure so as to present substantially the profile to the radiation in the different positions of the scanning structure to compensate for changes in the absorbing path length presented to the X-rays by the body and locating structure during the scanning movement,
wherein the locating structure is located in a fixed position during motion of the scanning structure.

Usually the source of radiation will be arranged to project the radiation across the aperture in many laterally spaced beam paths, which define chords in the aperture, the detecting means being arranged to provide separate output signals indicative of the amount of radiation transmitted along such paths. This can be achieved by collimating the radiation from the source so that it is confined to one beam path in the plane of examination and by scanning the source and detection means laterally in the plane, a lateral scan being executed for each small increment of rotation of the scanning structure. Alternatively the radiation from the source may be collimated to form a sectoral swath of radiation in the plane of the aperture, the angular subtense of the swath being sufficient to include the aperture. With either construction, the aforesaid attenuating mass would normally be shaped to compensate for different lengths of the various chordal path, which the radiation follows across the aperture. The attenuating mass preferably includes a solid member which is spaced from or moveable away from the locating structure so that the latter can be adjusted or replaced to accommodate different parts of the patient's body or patients of different sizes.

When reference is made herein and in the claims to the attenuating mass comprising a solid member, this is intended to mean that the attenuation occurs mainly in solid material, and does not necessarily mean that the member does not include cavities. The attenuating mass may also include liquid.

Figure 2:
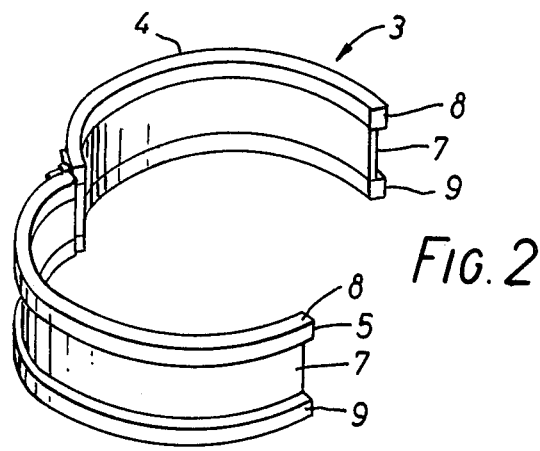
Figure 3:
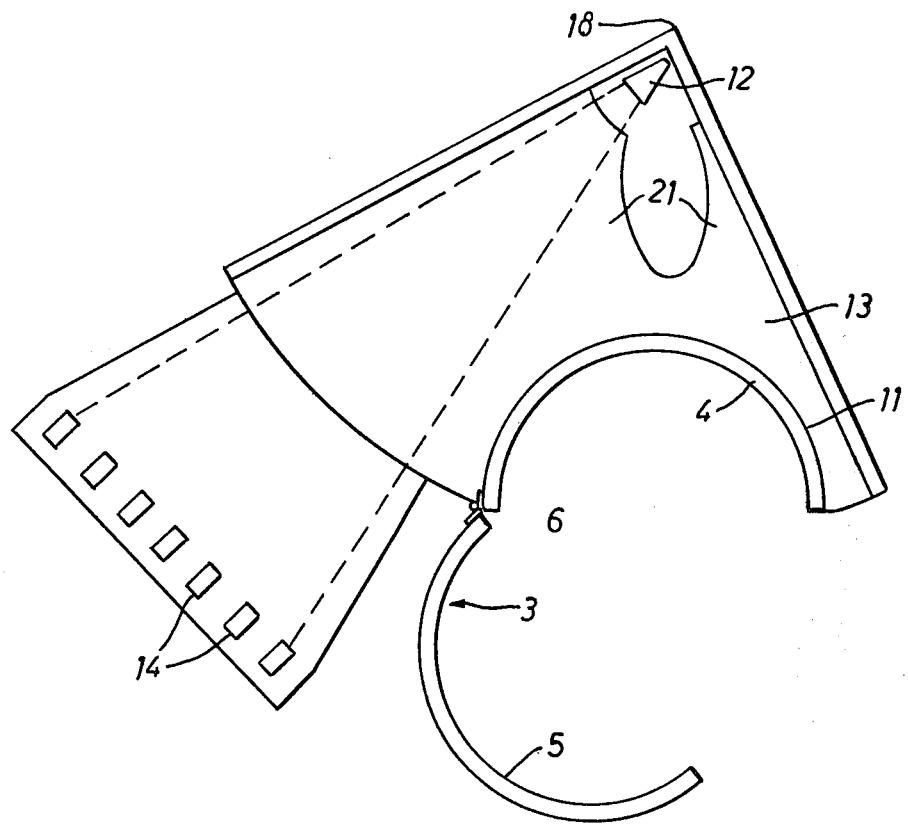
Figures 4A, 4B:
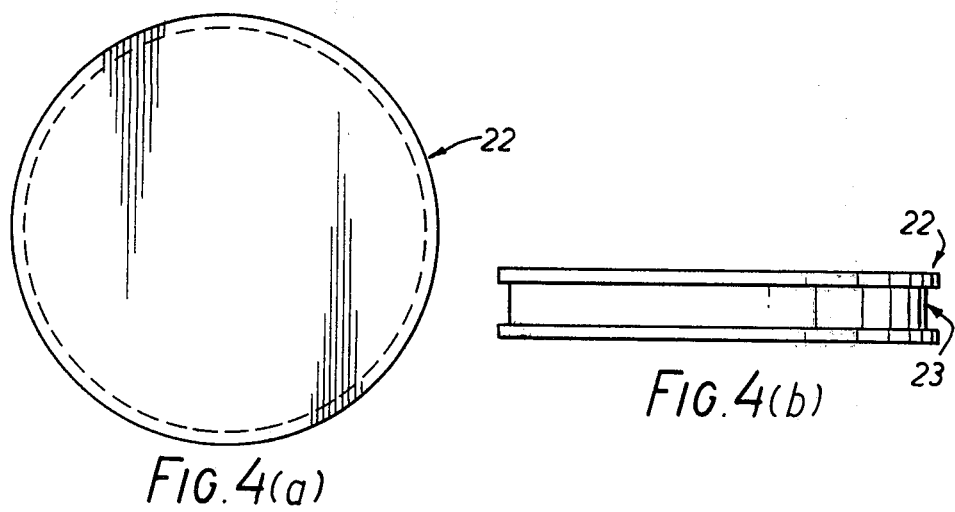
Figure 5:
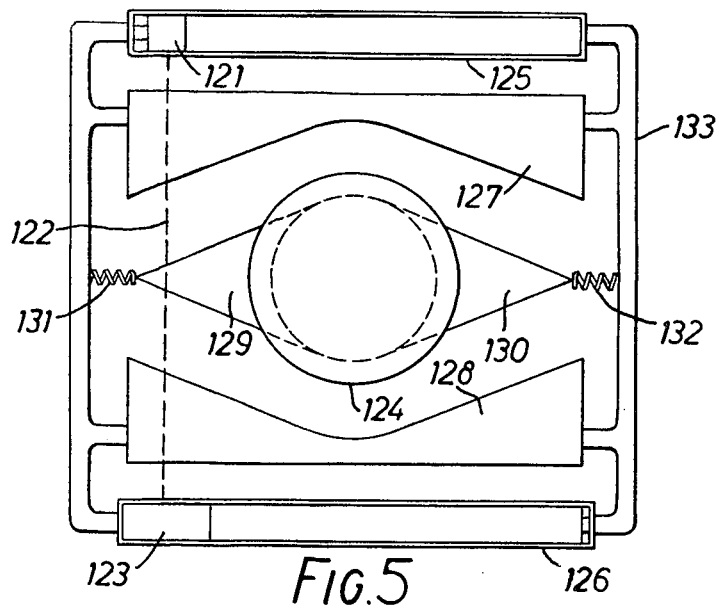
Figure 6:
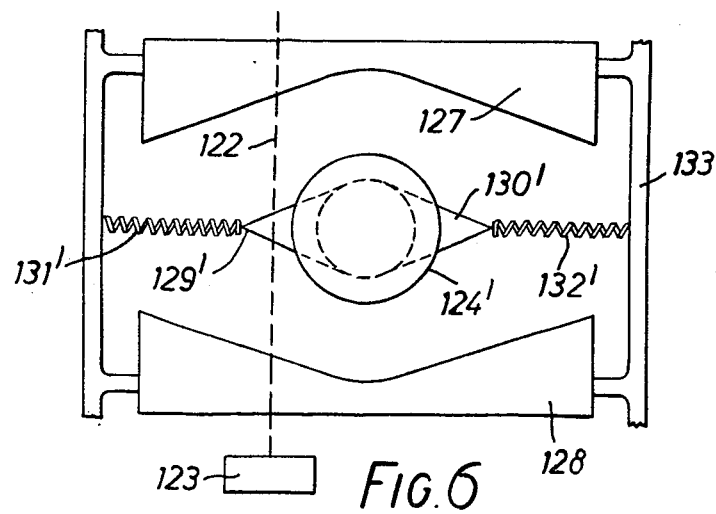
Figure 7:
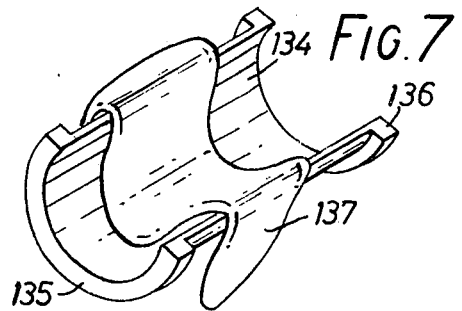
Figure 8:
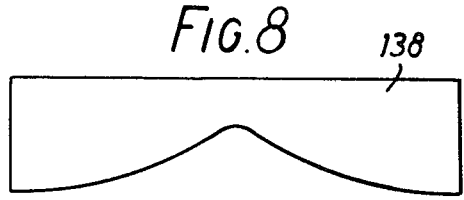

In order that the invention may be clearly understood and readily carried into effect, some embodiments thereof will now be described by way of example only with reference to the accompanying drawings of which:

FIG. 1 shows, schematically and in plan view, one example of radiographic apparatus in accordance with the invention, FIG. 2 shows, in perspective view, a clamping means suitable for use in the apparatus shown in FIG. 1, FIG. 3 shows, schematically and in plan view, another example of apparatus in accordance with the invention, FIGS 4(a) and 4(b) show in perspective view, a calibration disc which may be utilised instead of the calibration arrangements shown in FIGS. 1 and 3, FIG. 5 shows, in elevational view, yet another form of the present invention, FIG. 6 shows, in similar view, a portion of the apparatus of FIG. 5, adapted to accommodate a smaller body, FIG. 7 shows, in perspective view, part of a member which can be used to locate a body, and FIG. 8 shows a compensating member, and a modification to its shape which is useful in certain applications of the invention.

Referring now to FIG. 1, a tubular, flexible bag 1 containing water is wrapped around the region of interest of a body to be examined, so that the ends of the bag 1 overlap. The bag may be constructed, for example, of rubber and it is fitted tightly around the body 2 by deflating the bag and then re-filling it with water, so as to assume intimate contact therewith — excluding as much air as possible from the region between the bag 1 and the body 2. The overlapping ends of the bag 1 are secured together, for example by means of tapes (not shown) to hold the bag temporarily in position around the body and the bag is then clamped firmly in place with a clamping or locating means 3, which is shown in more detail in FIG. 2. The clamping means 3 comprises a pair of semi-circular members 4, 5 hingedly secured together as at 6. The members 4 and 5 each comprise a central band 7 and upper and lower flanges 8, 9 respectively; at least the central band of each member being formed of Perspex or another suitable plastics material. The hinge 6 has a part which links the upper flanges of members 4 and 5 and a part which links the lower flanges of said members; the arrangement being such that when the non-hinged ends of the two members are closed together, the central bands at the hinged ends of the two member abut closely. The clamping means 3 can be secured in its closed position by means of a clasp 10 which links the top and bottom flanges of the non-hinged ends of the members 3 and 4 but does not overlie the central band 7.

In fitting the clamping means 3 around the bag 1, the former is opened, placed so as to encircle the bag 1, (which, in turn, surrounds the part of the body 2 to be examined) closed and secured in position by means of the clasp 10. The inner diameter of the clamping means 3 and the amount of water contained in the bag 1 are chosen in accordance with the dimensions of the body part to be examined and it is arranged that, when the clamping means 3 is secured around the bag 1, the latter is urged against the body part 2 by pressure exerted all around it, thereby ensuring intimate contact between the bag 1 and the body part 2 and also providing sufficient grip to prevent the bag 1 moving relative to the body part.

This having been done, the body is then located within a circular aperture 11 in a radiographic scanning apparatus. The apparatus includes a source 12 of X- or γ- radiation, a divided, sectoral-shaped sheet 13 of Perspex which contains the aforementioned aperture 11, and a plurality of detectors 14 sensitive to the radiation produced by the source 12. The source 12 produces a sectoral swath of radiation indicated by the dotted outlines 12a, the angular subtense of the swath being sufficient to include the locating or clamping means 3 for the patient. The Perspex sheet 13 is extended on the left-hand side of the said aperture 11 (as viewed in FIG. 1) for calibration purposes as will be described in more detail hereinafter. The scanning apparatus is mounted on a rotatable, annular disc-like member 15 which is concentric with the aperture 11 and can be rotated, about an axis passing through the centre of the aperture, by means of a motor 16 which drives a gear wheel 17, the wheel 17 being adapted to co-operate with gear teeth (not shown) provided around the periphery of the disc-like member 15.

The source 12 and detectors 14 are moveable relative to the Perspex sheet 13 by means of a pivot 18, so that the detectors 14 can be swung, in their own plane, to occupy the position shown in dotted outline at 19. The source 12 also pivots through the same angle as the detectors 14 and this enables radiation to be passed from the source 12 to the detector 14 via the part of the Perspex sheet 13 which does not contain the aperture 11. This is useful for calibration purposes, since the relative performances of the various detectors when operated under substantially identical conditions to one another can be determined.

In normal operation, however, the source 12 and the detectors 14 occupy the respective positions shown in solid outline in FIG. 1.

In order to locate the body, which is surrounded by the water bag 1 and the clamping means 3, in the scanning apparatus, the internal diameter of the aperture 11 is formed with a tongue adapted to engage with the central band 7 of the clamping means 3. Moreover, the two parts of the sheet 13 are hingedly separable; the hinge being co-sited with the pivot 18. The two parts of sheet 13 are opened to permit the body with its surrounding water bag and clamp to be positioned within the aperture 11 (which is bisected by the dividing line between the two parts of the sheet 13). The two parts of sheet 13 are then closed together such that the aforementioned tongue engages with the central band 7 of the clamping means 3. Said clamping means 3 is then fixedly secured, for example by means of locating rods 20, to prevent it rotating with the member 15, and the process of irradiating the body from a plurality of different directions can commence. The aforementioned irradiation is carried out by rotating the member 15 step-wise (say by one degree at a time) or continuously through a total of about 180° (or 360°) and noting the radiation detected by the detectors 14 at successive angular positions.

When the scanning apparatus rotates, the tongue and the inner diameter of the aperture 11 acts as a bearing in the central band 7 of clamping means 3. Other bearing surfaces could, however, be provided if desired and moreover it will be appreciated that the whole apparatus may be suitably mounted in a vertical plane rather than in a horizontal plane as thus far described.

FIG. 3 shows part of the scanning apparatus, and the clamping means, of an alternative embodiment of the invention. Similar features are denoted by the same reference numerals as were used in FIG. 1.

In FIG. 3, in contrast to FIG. 1, the part of sheet 13 between the aperture 11 and the detectors 14 is omitted. In order to compensate for this, additional Perspex is provided, as shown at 21 between the source 12 and the aperture 11. The clamping or locating means 3 is shown in position in the aperture 11 although it contains no water bag and no body.

Although the clamping means 3 has been described herein as comprising two semi-circular members 4 and 5 which are hingedly secured together, it can be advantageous in some circumstances for the two members 4 and 5 to be separate and held together, when in position around the bag 1, by clasps such as 10 at both ends.

FIGS 4(a) and 4(b) show, in plan and elevational views respectively, a calibration disc 22 made, for example, of Perspex, which is dimensioned so as to fit into the aperture 11 in the scanning apparatus.

The disc 22 is provided with a peripheral channel 23 with which the aforementioned tongue formed on the internal surface of aperture 11 can engage. If a disc such as 22 is used, then the extended portion of the sheet 13 to the left of the aperture 11 can be omitted, thus saving in material. Moreover, if the disc 22 is fixed so that it does not rotate with radiation of the scanning apparatus, then the calibration can be carried out under pseudo-operational conditions. It will be understood that the sheet 13 or the parts thereof, constitute an attenuating mass shaped to compensate for different lengths of the various chordal paths which the radiation from the source 12 follows across the patients aperture to reach the detectors 14. The attenuating mass rotates with the structure which supports the source 12 and detectors 14, so that the same profile is always presented to the sectoral swath of radiation from the source.

The number of detectors 14 illustrated in FIGS. 1 and 3 is relatively small. In practice the number would be much larger. Each detector provides an output signal indicative of the transmission or absorption of the X-radiation from the source along a narrow beam path. The output signals from the detectors are utilised in reconstructing an image of the transmission or absorption of the elementary areas of the cross section of the body which is examined by the X-radiation. To achieve accuracy in the image reconstruction, outputs from many beams across the width of the swath, at many different angular positions of the scanning structure 12, 14, 15, are required. For this reason the detectors 14 are placed very close together in practice, and expedients may also be adopted for obtaining output signals from beams intermediate to those defined at any one time by the detectors 14.

The image reconstruction may be affected as described in our U.S. Pat. No. 3,778,614, or by methods involving convolution.

Referring now to FIG. 5, the apparatus illustrated therein includes a radiation source 121. The source 121 is arranged to generate a beam 122 of radiation. Mounted opposite the source 121 and disposed to receive the radiation therefrom is detector means which is sensitive to the radiation. Typically the detector means 123 comprises a sodium iodide or caesium iodide detector eptically coupled to a respective photomultiplier tube (not shown). The photomultiplier tube provides output signals which are indicative of the absorption suffered by the radiation from the source 121 on traversing a body (not shown) which is disposed within a — substantially cylindrical body locating structure 124 which will be more fully described hereinafter. In order to define the aforementioned beam, each of the detector means 123 receives the radiation via a respective collimator, not shown in the drawing.

The source 121 and the detector means 123 are linearly movable, in respective channels 125 and 126, relative to the body locating structure 124, so as to effect a translational scan of the radiation in a plane of interest through a body disposed in the structure 124.

Disposed between the source 1 and the body locating structure 124 on the one hand and between the structure 124 and the detector means 123 on the other hand are respective compensating or attenuating membes 127 and 128, these members being formed conveniently of the material known by the Registered Trade Mark "Perspex." The function of the members 127 and 128, in conjunction with two other compensating members 129 and 130 which are formed of the same material, is to present to radiation from the source 121 a substantially constant absorption or attenuation as the aforementioned translation scan occurs, when the body locating structure 124 is replaced by a homogeneous disc (not shown) of the same material as the compensating members. The parts 127, 128, 129 and 130 thus constitute an attenuating mass. This ensures that when the scanning is carried out with the body in place, variations in absorption, as represented by variations in the output signals from the photomultipliers, can be attributed to variations within the body. In some circumstances, as will be explained later, it is not possible to render the absorption in the absence of a body entirely constant across the lateral extent of the scan, and in these circumstances, a computer which is arranged to process the output signals is programmed to take variations in absorption, due to causes other than the body, into account when performing its operations upon output signals derived when the body is inserted.

The source 121, detector means 123 and compensating members 127 to 130 are arranged to rotate relative to the body locating structure 124, and they are thus supported in a common frame or structure 131 which is caused to rotate (usually step-wise) about an axis perpendicular to the plane of the beam 122 and passing through the body.

The members 129 and 130 are substantially in the form of isosceles triangles with concave bases, the concave bases being curved to fit the outer cylindrical surface of the body locating structure 124. The members 129 and 130 are resiliently urged towards the structure 124 by means shown schematically as a pair of compression springs 131 and 132. The plastics material of the members 129 and 130 has been found to slip readily on the surface of the structure 124 which is formed of aluminum without the need for special bearing surfaces.

A particular advantage of the apparatus shown in FIG. 5 is that differently sized bodies can be accommodated without the need for any movement of the source 121, the detector means 123, the frame 121 or the larger compensating members 127 and 128. All that is necessary is to remove the smaller compensating members 129 and 130, together with the associated springs, and to withdraw the body locating structure 124 axially. Suppose that a substantially smaller body is now to be investigated by the apparatus then, as shown in FIG. 6, the structure 124 is replaced by a suitably smaller container 124', the members 129 and 130 are replaced by smaller members 129' and 130' and larger spring members 132' and 133' are provided. The beam 122 shown in FIG. 6 at the leftwards extremity of its translational scanning motion for the smaller body, to indicate that, as in FIG. 5, there is an overscan which permits the source 121 and the detector means 123 to be disposed completely to one side of the body locating structure 124 (or 124') for calibration purposes. It will be observed that in FIG. 6 the straight sides of the members 129' and 130' are parallel to the sloping surfaces of the members 127 and 128, as are the straight sides of the members 129 and 130 in FIG. 6. The small arcuate portions of the members 127 and 128, however, are dimensioned to conform to the curvature of the outer surface of the body locating structure 124, which represents a container for a body of average size, so that when a smaller structure (such as 124') or a larger container is used, slight variations in absorption will occur in the middle of the translational scan due to the slight mismatch in curvature between the body container and the arcuate portions of members 127 and 128. Such variations, however, can be compensated for in the manner previously described and by suitable programming of the computer.

Although in operation of the apparatus the locating structure 124 is fixed relative to the scanning structurre, it can also occur that the body locating structure may not be located exactly centrally between the two members 127 and 128, and in these circumstances, the overscan positions at the left and right hand sides of the body container provide information indicative of this and the information so provided can be used to preprogramme the computer in such a way as to compensate for the lack of centrality.

For example, if in FIG. 6, the body locating structure is disposed to the left of the central position in which it is shown, then the overscan readings taken with the beam 122 completely to the left of the structure 124 will provide absorption readings higher than they should be because the member 129 will be displaced to the left, whereas the overscan readings taken with the swath completely to the right of the structure 124 will provide absorption readings lower than they should be, because the member 120 has been displaced to the left. These overscan readings are fed into the computer which is arranged to extrapolate linearly between them to effect compensations for each point across the lateral scan.

In a convenient arrangement, as shown in FIG. 7, the body locating structure 124 comprises two semi-cylindrical portions, one of which is shown at 134 and the other of which is not shown. The portions such as 134 are constructed of aluminum of thickness 0.020 inch and end rim portions 135, 136 0.5 inch thick are formed integrally therewith. The axial extent of the rim portions such as 135 is 0.25 inch. Within the portion 134 is laid a bag 137 which is either empty or contains a little water. The patient is laid upon the portion 134 so that the part of his body which is to be examined is over the bag 137. The free ends of the bag, which depend outside the portion 134 as shown, are then wrapped around the patient so that the ends overlap and the second cylindrical portion of the structure 124 is placed on top of the portion 124, so that corresponding parts abut, and secured thereto by any convenient means. Water is then pumped into the bag 137 until it fits tightly around the patient's body, so as to expel air from the region of interest, i.e. the region around the edge of the patient's body which is intersected by the plane of investigation.

The above procedure holds for examination most parts of a patient's body, but when a plane through the lungs is to be examined, large areas of the plane will comprise air and thus it has been found unnecessary to surround the body with water, since this expedient is used to reduce discontinuities in absorption suffered by the radiation on passing from the source to the detector means. The body locating structure may also be dispensed with in these circumstances and a pair of specially shaped members, one of which is shown at 138 in FIG. 8, are provided to replace the members 127 and 128 of FIGS. 5 and 6. The shaping of the members such as 138 is designed to allow for the fact that, on investigating a plane through the lungs, two large areas of air are usually separated by a continuous region of tissue in which the heart is situated. Thus in this central region, the thickness of the members such as 138 is reduced as compared with its thickness in regions which overlie the large areas of air, thus to minimise variations in absorption across a lateral scan in order to improve the resolution of the apparatus. When planes passing through the lungs are examined, the "zero" of the apparatus is made to correspond with the absorption of air, whereas when other planes through the body are investigated, the "zero" is made to correspond to the absorption of tissue — i.e., approximately, to the absorption of water. It is to be understood that the invention can be applied to many forms of apparatus with many diifferent beam scanning systems. Moreover, although scanning in a single plane alone has been indicated, simultaneously scanning in adjacent parallel planes may occur, using the same source and attenuating mass. It is also to be noted that some discretion must be exercised in the choice of the attenuating mass. In the interest of maintaining high accuracy the attenuating mass should be such that it does not excessively disturb the frequency spectrum of the penetrating radiation. Absorbing masses of water or many plastics are suitable.

I claim:
1. Apparatus for examining the body of a patient by means of penetrating radiation comprising:
   a. a ring-shaped locating structure adapted to enclose the part of the patient to be examined,
   b. a source of penetrating radiation,
   c. a detecting means sensitive to the radiation,
   d. a scanning structure, which is rotatable about an axis passing through the part of the patient enclosed by said locating structure, supporting said source and said detecting means so that the source can project radiation through the said part of the patient to be received by the detecting means,
   e. means for rotating said scanning structure about said axis so that the radiation can be projected through the body from a plurality of different directions in a plane substantially perpendicular to the said axis and,
   f. an attenuating mass not attached to and adapted to rotate around said locating structure on rotation of said scanning structure so as to present substantially the same profile to the radiation in the different positions of the scanning structure to compensate for changes in the absorbing path length presented to the X-rays by the body and locating structure during the scanning movement, wherein the locating structure is located in a fixed position during motion of the scanning structure.

2. Apparatus according to claim 1 in which the attenuating mass comprises a solid member which is held in contact with the outer surface of the ring-shaped locating structure and rotates there around on rotation of said scanning structure.

3. Apparatus according to claim 2 in which said solid member can be moved apart from said locating structure to facilitate the positioning of the patient or replacement of the locating structure.

4. Apparatus according to claim 1 wherein a deformable mass having an absorption similar to that of the body is positioned around the patient to fill gaps between the patient and said locating structure.

5. Apparatus according to claim 1 in which said locating structure is held in position during rotation of the scanning structure with the aid of said scanning structure.

6. Apparatus according to claim 1 in which said locating structure comprises a plurality of members which can be separated or opened to facilitate positioning of the patient.

7. Apparatus according to claim 1 in which said attenuating mass comprises solid material spaced from the locating structure and shaped to compensate for different path lengths for the radiation crossing the said locating structure.

8. Apparatus according to claim 1 in which said attenuating mass comprises at least one member spaced from said locating structure and two members which contact an outer surface of said locating structure at opposite sides thereof and which can be moved apart to allow removal and replacement of said locating structure.

9. Apparatus according to claim 1 in which said attenuating mass is located substantially wholly on the source side of the locating member.

* * * * *